United States Patent [19]

Floyd

[11] 4,027,735

[45] June 7, 1977

[54] BLOOD MIXING AND WEIGHT MONITORING APPARATUS

[75] Inventor: Johnnie E. Floyd, Austin, Tex.

[73] Assignee: Engineering & Research Associates, Inc., Tucson, Ariz.

[22] Filed: May 20, 1976

[21] Appl. No.: 688,400

[52] U.S. Cl. .............................. 177/118; 177/229; 177/DIG. 5; 177/DIG. 11
[51] Int. Cl.² ..................... A61B 5/14; G01G 13/30
[58] Field of Search .......... 177/118, 116, 168, 164, 177/229, 225, DIG. 5, DIG. 11; 128/214 E, DIG. 13

[56] References Cited

UNITED STATES PATENTS

| 3,698,494 | 10/1972 | Gaudin | 177/118 |
| 3,924,700 | 12/1975 | Lindsey | 177/118 |
| 3,960,224 | 6/1976 | Silvers | 177/116 X |

*Primary Examiner*—Joseph W. Hartary
*Attorney, Agent, or Firm*—Cahill, Sutton & Thomas

[57] ABSTRACT

Weight monitoring apparatus supports and agitates a fluid collection bag to mix a received flow of fluid with a fluid contained within the bag while simultaneously monitoring the increasing weight of the bag. When a predetermined weight of the bag and its contents is achieved, the inflow of fluid is automatically interrupted.

13 Claims, 10 Drawing Figures

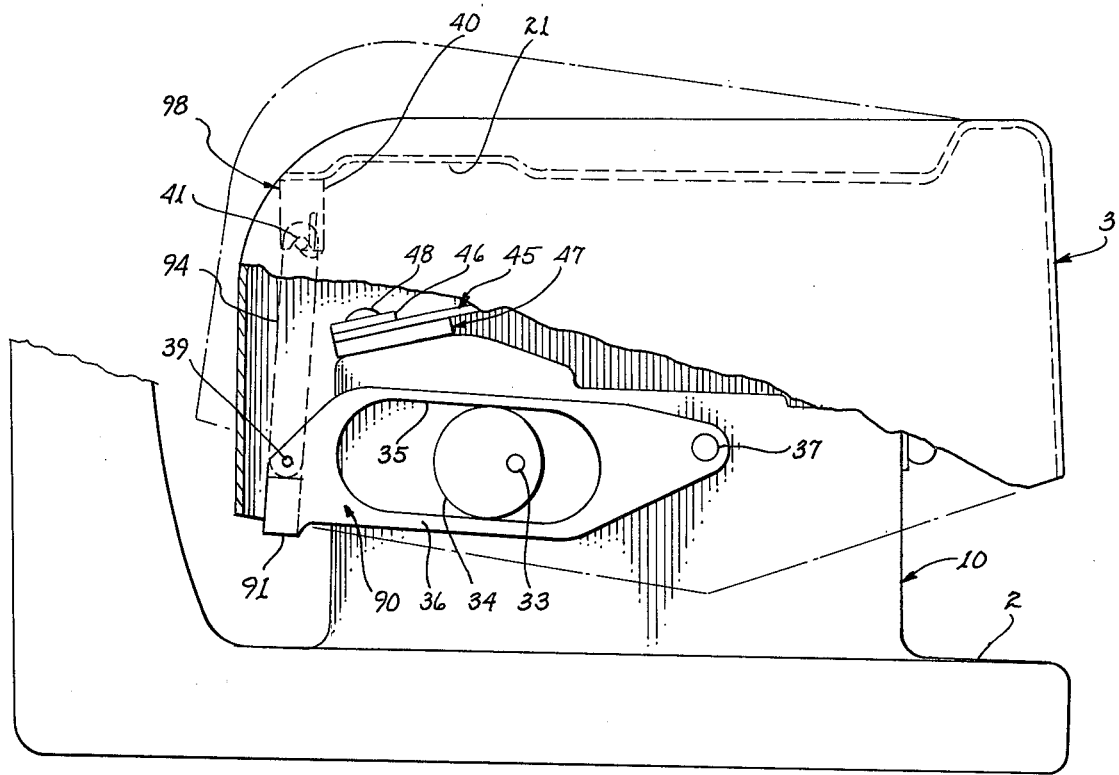
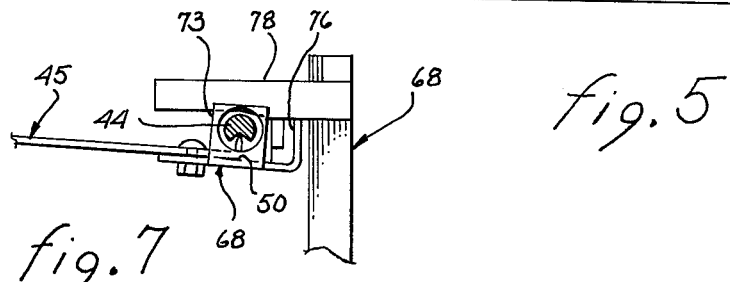
fig. 7
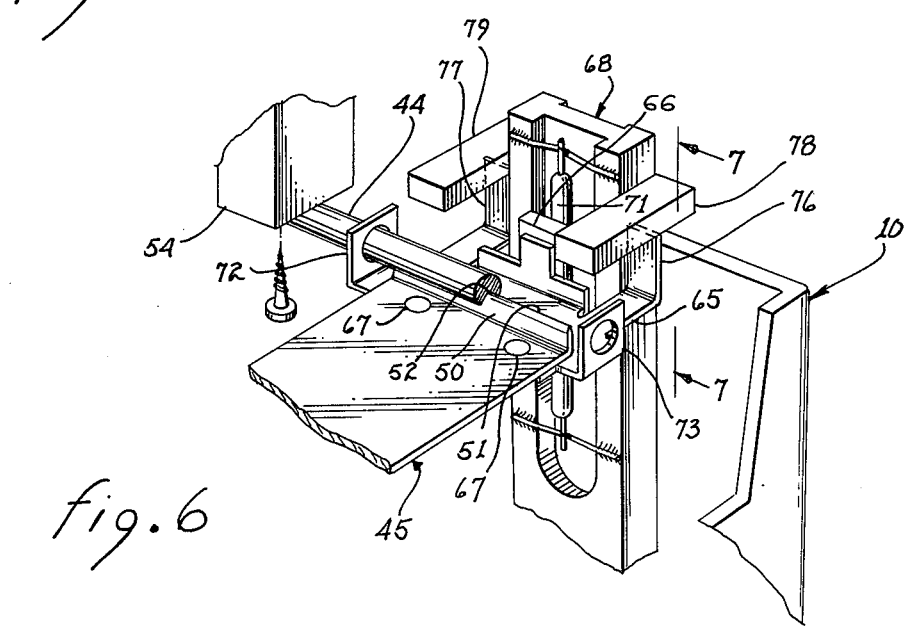
fig. 6

BLOOD MIXING AND WEIGHT MONITORING APPARATUS

The present invention relates to weighing apparatus and, more particularly, to apparatus for dynamically weighing a fluid flowing into a collection bag while agitating the bag to cause mixing of the fluid within the bag.

Presently existing techniques for collecting human blood in blood storage bags are relatively crude. In a widely used technique, a collection bag rests upon a table or is suspended from a stand and is connected to a blood donor by a tube. The blood flows into the collection bag in response to the pumping action of the donor's heart until the pressure within the bag prevents further inflow or until such time as an operator halts further flow. By either means of halting the blood flow, there is little uniformity in the weight of the blood collected. Moreover, as each collection bag contains a predetermined amount of preservative, the relationship of preservative to blood may not be at an optimum ratio because of the discrepancies inherent in the above described technique. Another technique incorporates the use of a static weighing scale to limit the amount of blood by weight flowing into a collection bag. As is well known to those familiar with static scales of less than excellent quality, the friction inherent in such scales often precludes an accurate determination of the weight of blood within each collection bag. Moreover, aging, humidity, temperature and other variables may vary the response of the scales on a short term basis. When such a static scale is used, the monitoring operation is generally performed by a technician simultaneously supervising several blood donors. Again, because the technician cannot continuously monitor each of the scales, some discrepancies arise because the blood flow may be interrupted prior or subsequent to collection of the predetermined weight.

In either of the above discussed techniques, there occurs only a happenstance mixing of the preservative with the inflowing blood. Some further mixing may occur during handling and/or transportation of the collection bags. The speculative nature of the mixing process sometimes results in decomposition of the blood to the extent that it is no longer fit for use. The detection of this condition is not always assured and may result in deterioration of the blood quality and the ultimate recipient of the blood or blood components may not obtain full benefit from a transfusion.

It is therefore a primary object of the present invention to provide apparatus for dynamically weighing a fluid flowing into a container.

Another object of the present invention is to provide apparatus for collecting a predetermined weight of fluid with a dynamic weighing scale while simultaneously agitating the fluid.

Still another object of the present invention is to provide apparatus for automatically terminating the flow of fluid into a container as the container achieves a predetermined weight.

Yet another object of the present invention is to provide a means for accurately limiting the total weight of a fluid flowing into a container while the container is agitated.

A further object of the present invention is to provide a means for filling a series of blood collection bags with an essentially equal weight of blood.

A yet further object of the present invention is to provide an easily portable weight monitoring and agitating apparatus for filling blood collection bags with a predetermined weight of blood.

These and other objects of the present invention will become apparent to those skilled in the art as the description thereof proceeds.

The present invention may be described with greater specificity and clarity with reference to the following figures, in which:

FIG. 5 is a partial cutaway view of the present invention and illustrates the operation of the rocker mechanism.

FIG. 6 is a detailed perspective view of a knife edge pivot point and reed switch assembly.

FIG. 7 is a side view of the leaf spring bumper and bar assembly.

Figure 1:
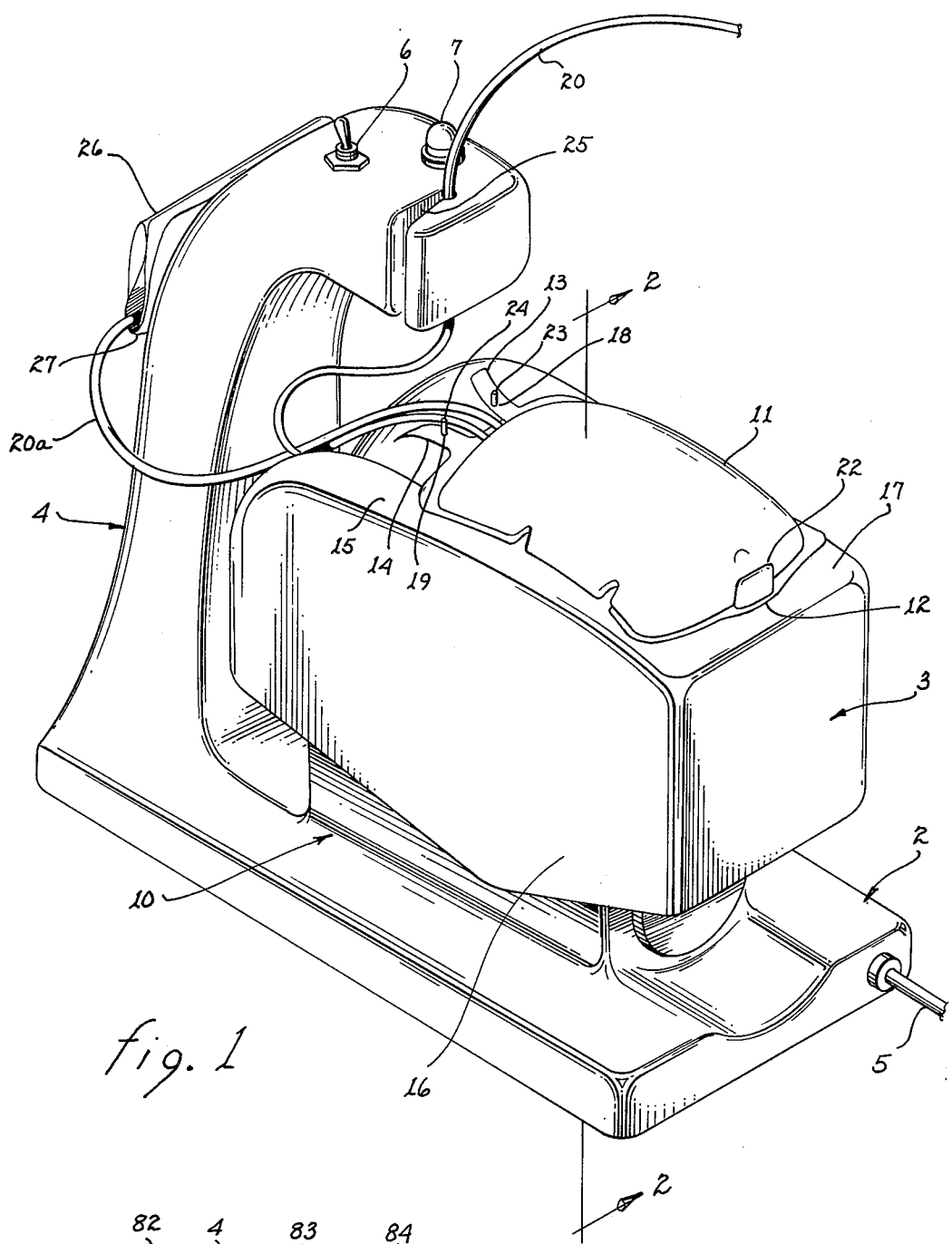
FIG. 1 is a perspective view of an embodiment incorporating the present invention.

Referring now to FIG. 1, there is illustrated a rocker and weight monitoring apparatus 1 having a pedestal 4 and a base 2 with an upwardly extending foundation 10 for supporting a rocker 3. An electrical power cord 5 extends into base 2 to provide electrical power via on/off switch 6 to the electrical motive means and electrical components. A visual indicator, such as light 7, or an audible indicator, such as a bell, may be employed to indicate whether or not the apparatus has terminated the fluid flow. Foundation 10 indirectly supports rocker 3 and houses an electrical motor for actuating the rocker.

Rocker 3 is formed with a generally horizontal surface 15 laterally terminated by a downwardly extending shroud 16, which shroud encircles foundation 10. A tray or depression 17, configured to conform with and receive blood collection bags 11, is disposed within surface 15. Standard blood collection bags are presently manufactured with a loop 12 disposed at one end thereof and a pair of tabs 13 and 14 disposed at the opposite end. Registration apertures 18 and 19 are formed within the respective tabs during the manufacturing process of the collection bag and all dimensions of the collection bag are keyed thereto. One or more conduits 20 extend into the cavity of the collection bag intermediate tabs 13 and 14, thereby to provide a channel for the flow of fluid into and out of the collection bag.

For reasons which will become apparent as the description of the present invention proceeds, the positioning of collection bag 11 with respect to rocker 3 is relatively important in order to monitor accurately the weight of the inflowing fluid. A post 22 is disposed at one end of depression 17 to penetratingly receive loop 12. A pair of posts 23 and 24 extend upwardly from surface 15 to receivingly engage apertures 18 and 19, respectively, to effect registration of the collection bag with respect to the rocker. In summary, apertures 18 and 19 position collection bag 11 within depression 17 and loop 12 engages post 22, to prevent shifting of the collection bag due to the rocking motion of rocker 3.

Conduit 20, conveying a fluid such as blood, is mounted within a slot 25 disposed in pedestal 4. A solenoid actuated mechanism is disposed in proximity to slot 25 to pinch conduit 20 and prevent further fluid flow therethrough when collection bag 11 has become filled to a predetermined weight.

For certain purposes, a standby collection bag 26, in fluid communication with collection bag 11 through conduit 20a, may be employed. A retainer 27 is mounted upon pedestal 4 to secure bag 26 thereto until needed.

The primary operating mechanisms will be described with joint reference to FIGS. 1, 2, 4 and 5. An electrical motor 31 is mounted upon the interior surface of foundation 10. It receives electrical power directly from on/off switch 6 or a module 30 wherein the applied electrical power has been transformed to a different voltage level, current limited or otherwise regulated. The armature of electric motor 31 is operatively connected to a gear box 32 to drive an output shaft 33. A cam 34 is secured to shaft 33 whereby the cam will rotate in response to energization of electric motor 31. Alternately, a direct drive system without a gear box may be employed.

A U-shaped frame 90 is formed by a torsion bar 91 interconnecting cam follower 36 and arm 55. The ends of the cam follower and the arm are pivotally attached to foundation 10 through shaft 37 extending outwardly from opposed walls of the foundation. Slot 35 of cam follower 36 straddles cam 34. Because of the eccentricity of cam 34, U-shaped frame 90 will reciprocally pivot about shaft 37 within the vertical plane through a predetermined arc. The lower edge of vertically oriented trapezoidally shaped plate 94 is pivotally attached to frame 90 by means of a shaft 39. The upper edge of plate 94 is pivotally attached by a shaft 41 to legs 40 and 60 of a bracket 98 depending from interior surface 21 of rocker 3.

Rocker 3 is also supported by and positioned with respect to foundation 10 by means of a leaf spring 45. The base of the leaf spring is secured to a commensurately configured section of foundation 10 by means of a pair of plates 46 and 47 and bolts 48 and 49. Plate 47 is made of a material of sufficient hardness to prevent significant deformation by any stresses applied by leaf spring 45. Thus, alteration of the effective length (and hence spring constant) of the leaf spring is prevented.

Referring also to FIGS. 6 and 7, the free end 50 of leaf spring 45 is turned upwardly with the edge thereof honed for forming a knife edge 51. A female knife edge 52, which is a sharp cornered groove, is formed within rod 44. Knife edge 51 and female knife edge 52 are machined or otherwise fabricated so as to engage one another with minimum torque during relative pivotal movement therebetween. Rod 44 is attached to rocker 3 by screws extending into supports 53 and 54 located internal to the rocker. An extension 65 is attached to free end 50 of leaf spring 45 by means of bolts or rivets 67. Cages 72 and 73 are formed within laterally positioned flanges extending upwardly from the extension. These cages encircle rod 44 and permit limited vertical displacement of the rod with respect to extension 65 and knife edge 51.

From the above description, it may be appreciated that rocker 3 is pivotally supported upon leaf spring 45.

Moreover, reciprocating pivotal movement of the rocker with respect to the foundation is obtained by rotation of cam 34. That is, cam 34 will produce an oscillatory motion of frame 90 through interaction with cam follower 36, which oscillatory motion produces essentially only vertical translational movement of plate 94. The translational movement of plate 94 results in a reciprocating upward and downward movement of bracket 98 and the attached end of rocker 3 with essentially no horizontal movement of the rocker. The lack of horizontal or lateral movement of the rocker precludes forced lateral movement of the knife edge and encourages optimal torque coupling at the male and female knife edges. As the rocker is pivotally supported by knife edge 51, the reciprocating vertical movement of one end of rocker 3 induces rocking motion of the rocker about the knife edge. Hence, the above described motor driven linkages obviate weight monitoring inaccuracies which might result from forced reciprocal lateral displacement of the collection bag as well as inaccuracies introduced by the application of lateral forces to the coupled groove and knife edge.

As blood collection bag 11 fills, the weight acting upon leaf spring 45 increases. The increasing weight tends to deflect the leaf spring downwardly. Referring now specifically to FIGS. 2, 4, 6 and 7, the means for detecting a predetermined weight of the collection bag corresponding to a predetermined amount of deflection of the leaf spring will be described.

A slide 68 is slidably retained adjacent the interior surface of one end of foundation 10 by means of a bolt 69 threadedly engaging the slide and extending through guide slot 70. Generally horizontally oriented bars 78 and 79 are attached to the upper extremity of slide 68. Each of the bars protrude beyond bumpers 76 and 77, which bumpers extend upwardly from extension 65. Thereby, the upward movement of the bumpers and hence the upward movement of extension 65 is limited by bars 78 and 79.

Upon application of lifting force to rocker 3, the end of the rocker attached to plate 94 cannot be displaced independent of base 2. At the other end of the rocker, rod 44, attached thereto, will contact cages 72 and 73, which cages are raised. As the cases are a part of extension 65, it will be raised until bumpers 76 and 77 come into contact with bars 78 and 79. The bars restrict further upward movement of the bumpers and the attached extension. Thus, only limited upward movement of one end of the rocker independent of base 2 is possible. Nominally, such upward movement of the rocker permits disengagement of the male and female knife edges but the separation therebetween is limited to the extent that reengagement will occur upon removal of the lifting force.

Figure 2:
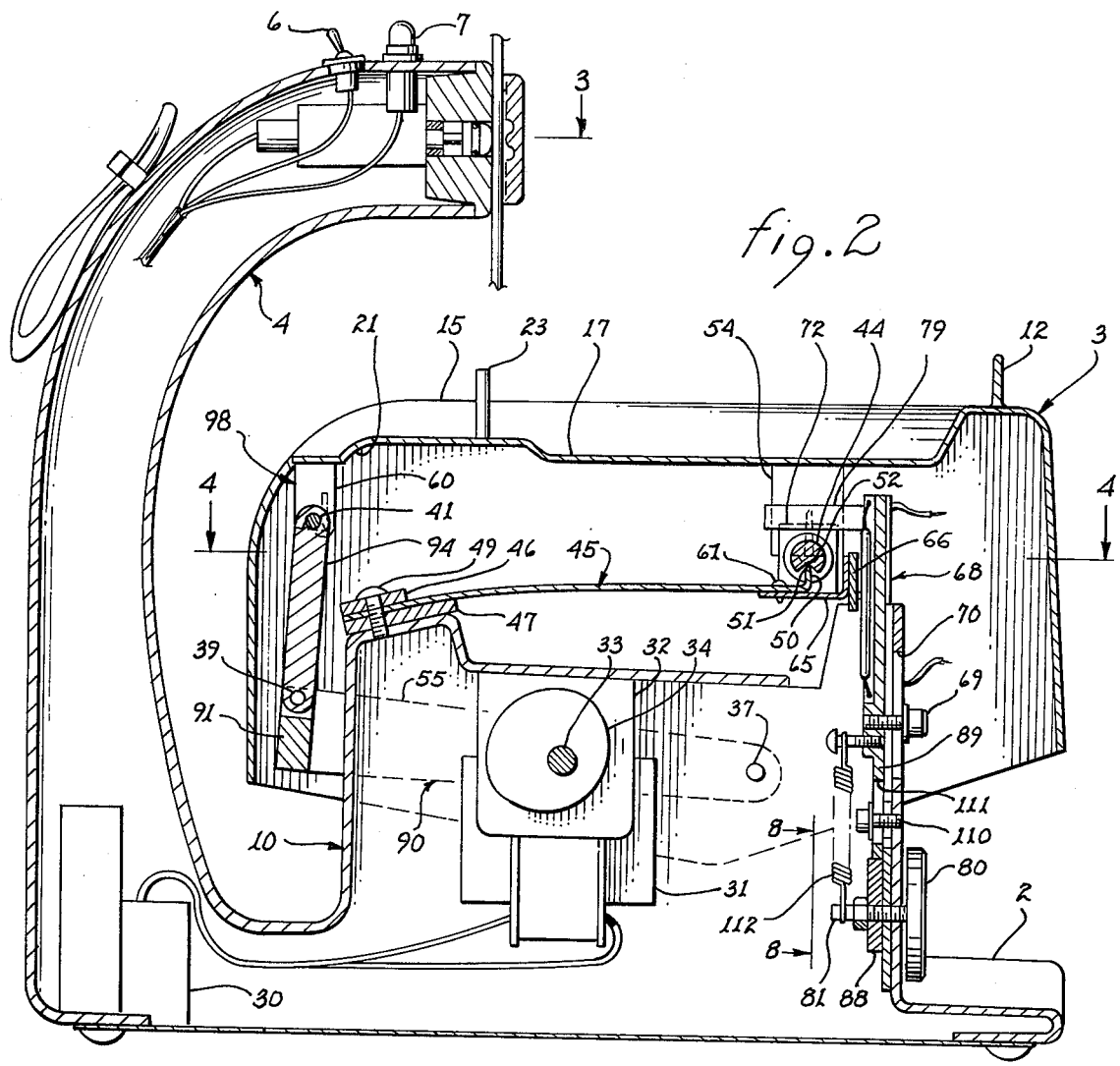
FIG. 2 is a cross-sectional view of the present invention taken along lines 2—2, as shown in FIG. 1.
Figure 4:
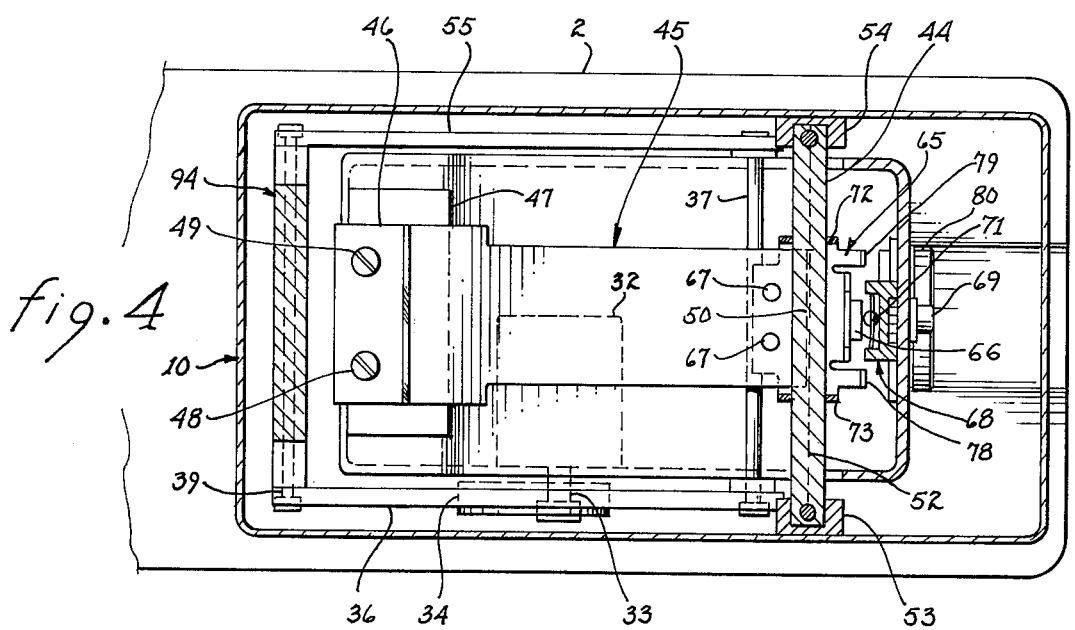
FIG. 4 is a cross-sectional view of the present invention taken along lines 4—4, as shown in FIG. 2.
Figure 8:
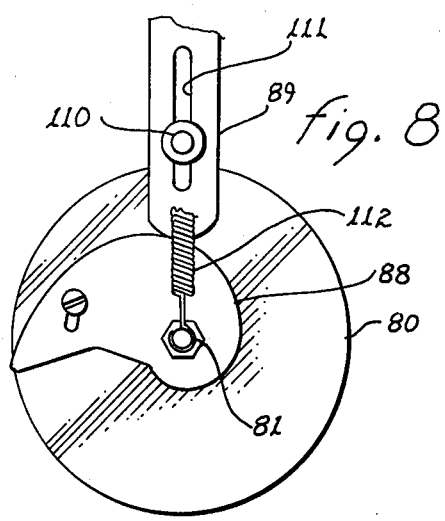
FIG. 8 is a detailed view of the manually adjustable slide cam.

Turning now to FIGS. 2, 4 and 8, the vertical position of the slide is controlled by means of a manually rotatable knurled knob 80 located external to foundation 10. A shaft 81 extends from knob 80 interior to the base and supports a cam 88. The cam supports a cam follower 89 attached to slide 68. A guide pin 110 penetrating slot 111 restrains lateral movement of the cam follower while accommodating vertical translation. A spring 112 biases the cam follower, and slide 68 toward cam 88. By turning knob 80, the cam rotates and causes the cam follower to move vertically and resulting in vertical repositioning of the slide. Downward repositioning of the slide results in downward repositioning of bars 78 and 79. Downward movement of the bars, upon contacting bumpers 76 and 77, will deflect free end 50 of the leaf spring downwardly and pre-load the leaf spring. Thus, knob 80 repositions slide 68 to establish any predetermined preloading of the leaf spring.

A magnet 66 is secured to extension 65. A generally vertically aligned magnetically responsive reed switch 71 is attached to the upper end of slide 68. The vertical spacing between the magnet and the reed switch is selected such that a predetermined amount of deflection of the leaf spring with respect to the slide must occur before magnet 66 is in sufficient proximity to the reed switch to actuate it. Thus, in order for the reed switch to be actuated, the blood collection bag must first acquire sufficient weight of blood to overcome any pre-loading of the leaf spring established by the vertical position of the slide and second, acquire an additional weight of blood to deflect the leaf spring with respect to the slide by the predetermined degree to position the magnet into operative engagement with the reed switch.

Figure 3:
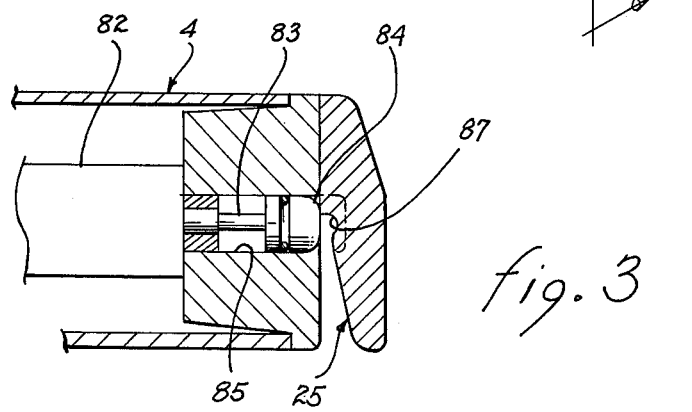
FIG. 3 is a cross-sectional view of the fluid flow cut-off apparatus taken along lines 3—3, as shown in FIG. 2.

FIG. 3 illustrates a mechanism for terminating the flow of fluid through conduit 20 whenever the blood collection bag has been filled with a predetermined amount of blood. A solenoid 82 is mounted within pedestal 4. Plunger 83 of the solenoid is attached to a piston 84 which is translatable within a cylindrical cavity 85. A conduit receiving passageway 87 is disposed within slot 25 (see FIG. 1).

When a blood collection bag is to be filled, conduit 20 is positioned within passageway 87 of slot 25. On actuation of reed switch 71 by magnet 66, solenoid 82 will be energized and plunger 83 is extended. Extension of the plunger produces a commensurate movement of piston 84. The piston squeezes conduit 20 against the wall of passageway 87 and prevents further fluid flow therethrough. Hence, further filling of the collection bag is inhibited.

To collect a fluid, such as blood, by using the present invention, the following steps may be employed. A collection bag to be filled is placed within the tray or depression 17 and correctly positioned therein by engaging the apertures of tabs 13 and 14 with posts 23 and 24, respectively. Loop 12 is inpaled upon stud 22 to prevent shifting of the collection bag during the filling operation. Conduit 20 in inserted within passageway 87 of slot 25 and ultimately connected to the source of the fluid. Switch 6 is placed in the "on" position to energize motor 31 and produce a rocking motion of rocker 3. The rocking motion will cause a mixing of the fluid within the collection bag. If blood is to be collected, a preservative is disposed within each collection bag to prevent decomposition of the blood until it can be properly stored or processed.

The inflowing fluid necessarily increases the weight of the collection bag. A shift in center of gravity of the collection bag during filling thereof will occur as a result of the reciprocating pivotal movement of the rocker about the knife edge. The shift in center of gravity cyclically lengthens and shortens the movement arm of the deflecting force acting upon the leaf spring.

Figure 9:
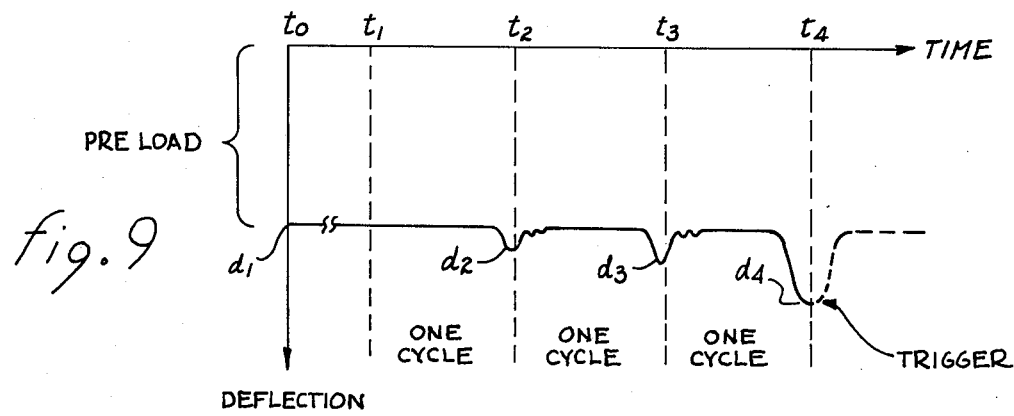
FIG. 9 is a graph of the leaf spring deflection.
Figure 10:
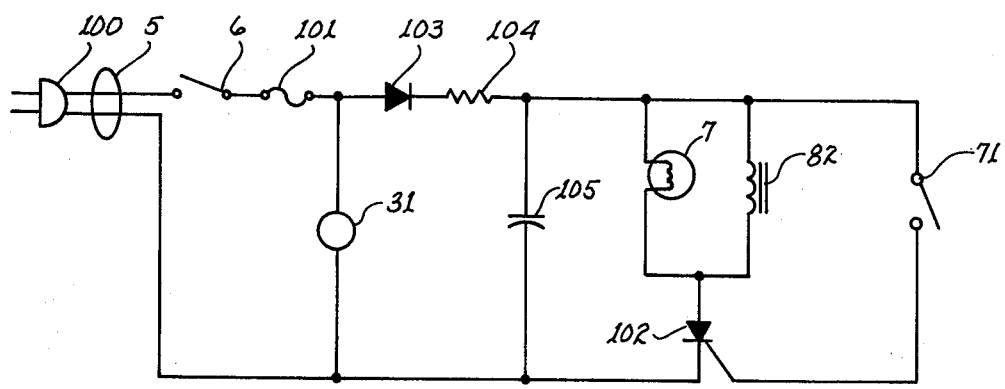
FIG. 10 is a representative circuit diagram.

Further description of the operation will be made with reference to the plot of deflection versus time depicted in FIG. 9. Until the weight of the blood collection bag and its contents reach a value equivalent to the pre-loading of the leaf spring ($d_1$), no intermittent deflection of free end 50 will occur, as indicated during the period $t_0$ to $t_1$. At time $t_1$, the weight has increased to the value of the pre-load and at the end of that cycle, $t_2$, the shift in center of gravity of the blood toward slide 68, induced by the rocking of rocker 3, will increase moment arm of the downward force sufficient to cause a slight deflection of free end 50, denoted by $d_2$, and attendant separation between bumpers 76, 77 and bars 78, 79. As the rocker 3 begins to rock in the opposite direction, the shift in center of gravity will reverse and the deflection is decreased until the bumpers again contact the bars and damp out vibration of the leaf spring free end. At time $t_3$, more blood will have flowed into the collection bag and the further weight increase causes a greater deflection $d_3$ of the leaf spring, which deflection is again aided by the increased moment arm of the downward force resulting from the shift in center of gravity of the collected blood. At time $t_4$, the weight has increased again and the resulting deflection $d_4$ is further increased, which deflection is sufficient to place magnet 66 attached to extension 65 into operative engagement with read switch 71. On actuation of the reed switch, solenoid 82 is energized causing plunger 83 to extend. Extension of plunger 83 forces the base of element 86 to squeeze conduit 20 and prevents further blood flow therethrough. Furthermore, the closing of reed switch 71 may also be used to de-energize electric motor 31 or to insert a time delay to cause de-energization thereof after a predetermined time period. To assist an operator in determining when the collection bag has been filled, light 7 may be de-energized or energized by the closing of reed switch 71; the choice in the state of the light switch is essentially a matter of human factor's engineering.

A simplified schematic of the electrical components is illustrated in FIG. 8. A standard wall plug 100 connects power cord 5 to a source of alternating current. A protective device, such as fuse 101, may be incorporated. On closing of switch 6, electric motor 31 is energized and the rocker will begin to rock. At such time as reed switch 71 is closed, triac 102 will begin to conduct and current will flow through diode 103, voltage dropping resistor 104, light 7 and solenoid 82. A bypass capacitor 105 precludes the flow of any alternating current to triac 102.

Modifications of the present invention are also contemplated. In example, a further function switch may be incorporated whereby motor 31 is not energized until after a predetermined weight increase has resulted by the fluid flowing into the collection bag. Thereafter, energization of the motor will occur to produce rocking motion or rocker 3 and the attendant mixing of the fluid(s) within the collection bag. As alluded to above, additional modes such as deenergizing the electric motor commensurate with actuation of the reed switch or at a predetermined time thereafter are also feasible.

The low friction attendant the male and female knife edges and the imposed pivotal movement therebetween provides a high degree of resolution in monitoring the increasing weight of the collected fluid. Thereby, a degree of accuracy is achievable which would otherwise be prohibitively expensive with presently available weighing devices. By experimentation, it has been found that the weight of fluid collection can be maintained within plus or minus two grams, which limits are well within acceptable levels for blood collection services. The mechanisms employed are relatively straight forward and require only normal tolerance levels, which parameters permit the present invention to be relatively inexpensive.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

I claim:

1. A dynamic weight monitoring apparatus for collecting a predetermined weight of fluid flowing into a collection bag while the collection bag is rocked to mix the collected fluid and including a base for supporting said apparatus upon a surface and a foundation extending upwardly from the base, said apparatus comprising in combination:
   a. a rocker for receiving and retaining the collection bag in fixed relationship thereto;
   b. weight responsive means having one end secured to the foundation and another end extending from the foundation for supporting said rocker, said other end of said weight responsive means being deflectable in the vertical plane in response to any change in weight of the contents of the collection bag;
   c. pivot means disposed intermediate said other end of said weight responsive means and said rocker for accommodating reciprocating angular movement of said rocker with respect to the foundation;
   d. motor driven linkage means disposed intermediate the foundation and said rocker for imparting a reciprocating vertical movement to one end of said rocker and producing a rocking motion of said rocker about said pivot means;
   e. position sensing means extending from the foundation for detecting a predetermined downward deflection of said other end of said weight responsive means, which deflection is commensurate with the weight of a predetermined quantity of fluid that has flowed into the collection bag; and
   f. indication means responsive to said sensing means for indicating that the predetermined quantity of blood has flowed into the collection bag.

2. The apparatus as set forth in claim 1 wherein said weight monitoring apparatus comprises a leaf spring.

3. The apparatus as set forth in claim 2 wherein said pivot means comprises a male and female knife edge.

4. The apparatus as set forth in claim 3 wherein said male knife edge extends upwardly from said other end of said weight responsive means and said female knife edge extends downwardly from said rocker.

5. The apparatus as set forth in claim 3 including a clamp for clamping the tube in response to actuation of said reed switch.

6. The apparatus as set forth in claim 5 wherein said clamp is mounted within a part of said apparatus.

7. The apparatus as set forth in claim 6 wherein said indication means comprises an electrically operated light energized by actuation of said reed switch.

8. The apparatus as set forth in claim 1 wherein said position sensing means comprises a magnet attached to said other end and a magnetically responsive reed switch attached to the foundation, said reed switch being actuated in response to a predetermined proximity to said magnet.

9. The apparatus as set forth in claim 8 including a vertically positionable slide for retaining said reed switch and cam means for positioning said slide at a predetermined location.

10. The apparatus as set forth in claim 1 wherein said linkage means comprises: a frame pivotally attached to the foundation, a motor driven cam acting upon said frame for inducing reciprocating pivotal motion of said frame, and a plate pivotally interconnecting said frame and one end of said rocker for translating pivotal movement of said frame into vertical movement of said one end of said rocker and producing rocking movement of said rocker about said pivot means without restraining downward deflection of said pivot means.

11. The apparatus as set forth in claim 10 including cage means for accommodating limited upward movement of said rocker with respect to the base while reengageably separating said pivot means.

12. The apparatus as set forth in claim 11 including means for pre-loading said weight responsive means whereby no deflection of said weight responsive means occurs until the weight of the collection bag increases to a value commensurate with the pre-loading.

13. The apparatus as set forth in claim 12 wherein said position sensing means includes magnetically responsive means for sensing only a weight greater than the pre-loading of said weight responsive means.

* * * * *